United States Patent
Lucido et al.

(12) 
(10) Patent No.: US 6,207,056 B1
(45) Date of Patent: *Mar. 27, 2001

(54) METHOD FOR BIOLOGICAL PURIFICATION

(75) Inventors: John A. Lucido, Mt. Sinai; Daniel Keenan, Rockville Centre; Eugene T. Premuzic, East Moriches; Mow S. Lin, Rocky Point; Ludmila Shelenkova, Yaphank, all of NY (US)

(73) Assignee: Brookhaven Science Associates, Upton, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/494,686

(22) Filed: Jan. 31, 2000

Related U.S. Application Data

(63) Continuation of application No. 09/199,241, filed on Nov. 24, 1998, now abandoned, which is a continuation of application No. 08/867,946, filed on Jun. 3, 1997, now Pat. No. 5,840,182, which is a continuation of application No. 08/613,125, filed on Mar. 8, 1996, now abandoned.

(51) Int. Cl.$^7$ ........................................................ C02F 3/00
(52) U.S. Cl. ........................... 210/608; 210/610; 435/262
(58) Field of Search ................................... 210/606, 610, 210/611, 620, 631, 138, 202, 205, 209, 258, 259, 532.2, 538, 608; 435/262, 262.5

(56) References Cited

U.S. PATENT DOCUMENTS

| | | | |
|---|---|---|---|
| 3,145,087 | 8/1964 | Walker | 23/272.6 |
| 3,577,678 | 5/1971 | Burton | 47/58 |
| 3,617,538 | 11/1971 | Bogert | 210/12 |
| 3,864,090 | 2/1975 | Richards | 23/267 |
| 4,237,003 | 12/1980 | El-Sayed | 210/606 |
| 4,666,606 | 5/1987 | Heinicke | 210/632 |
| 4,670,149 | 6/1987 | Francis | 210/608 |
| 4,810,385 | 3/1989 | Hater et al. | 210/606 |
| 4,882,059 | 11/1989 | Wong et al. | 210/606 |
| 4,891,136 * | 1/1990 | Voyt | 210/610 |
| 4,925,564 | 5/1990 | Francis | 210/608 |
| 4,940,539 | 7/1990 | Weber | 210/149 |
| 4,940,544 * | 7/1990 | Gode et al. | 210/608 |
| 4,992,174 * | 2/1991 | Caplan et al. | 210/610 |
| 5,171,687 | 12/1992 | Moller et al. | 435/286 |

(List continued on next page.)

OTHER PUBLICATIONS

Koch, Arthur L., "Bacterial Growth", McGraw–Hill Encyclopedia of Science and Technology, vol. 2, pp. 364–366. 7th Edition (1992).

*Primary Examiner*—Christopher Upton
(74) *Attorney, Agent, or Firm*—Margaret C. Bogosian

(57) ABSTRACT

An apparatus is disclosed for containing a microorganism culture in an active exponential growth and delivering a supply of microorganisms to an environment containing wastes for bio-augmenting the biodegradation of the wastes. The apparatus comprises a bioreactor and an operably connected controller. The bioreactor has a bioreactor chamber for containing a supply of microorganisms, a second chamber for containing a supply of water and inorganic nutrients, and a third chamber for containing a supply of organic nutrients. The bioreactor is operably connected to the controller in which a first pump is operably connected in fluid communication between the bioreactor chamber and the second chamber and third chamber, and a second pump is operably connected in fluid communication between the bioreactor chamber and the environment containing wastes to be biodegraded. The controller further includes a timer and regulator operably connected to the first and second pumps to effectively maintain the microorganisms in exponential growth in the bioreactor chamber and to deliver microorganisms to an environment to be treated. Also, disclosed is a method for bio-augmenting the biodegradation of wastes.

4 Claims, 6 Drawing Sheets

::::

U.S. PATENT DOCUMENTS

| | | | |
|---|---|---|---|
| 5,225,083 | 7/1993 | Pappas et al. | 210/606 |
| 5,227,068 * | 7/1993 | Runyon | 210/610 |
| 5,271,829 | 12/1993 | Heppenstall | 210/127 |
| 5,288,407 | 2/1994 | Bodwell et al. | 210/617 |
| 5,314,619 * | 5/1994 | Runyon | 210/610 |
| 5,340,376 | 8/1994 | Cunningham | 71/6 |
| 5,366,891 * | 11/1994 | Premuzic et al. | 435/262.5 |
| 5,516,687 * | 5/1996 | Perez et al. | 210/608 |
| 5,531,898 * | 7/1996 | Wickham | 210/611 |

* cited by examiner

METHOD FOR BIOLOGICAL PURIFICATION

This is a continuation of application Ser. No. 09/199,241 filed Nov. 24, 1998, now abandoned, which in turn is a continuation of application Ser. No. 08/867,946 filed Jun. 3, 1997, now U.S. Pat. No. 5,840,182 issued Nov. 24, 1998, which in turn is a continuation of application Ser. No. 08/613,125 filed Mar. 8, 1996, now abandoned.

This invention was made with Government support under contract number DE-AC02-76CH00016, between the U.S. Department of Energy and Associated Universities, Inc. The Government has certain rights in the invention.

BACKGROUND OF THE INVENTION

The present invention relates to an apparatus and method for biological purification of wastes. More particularly, the invention is directed to an apparatus and method for treatment of wastes, such as grease and other contaminants contained in waste water streams, ground water, soil, etc., by introducing living organisms to biodegrade the wastes.

Wastes, under normal conditions, are gradually broken down or biodegraded by indigenous microorganisms in the environment. However, biodegradation reactions are often hindered by environmental fluctuations such as changes in temperature, pH, salinity, water and air supply, etc. For example, wastes such as fat and grease are biodegraded by microorganisms to fatty acids and glycerol. In the presence of oxygen the fatty acids are further metabolized with the end product being carbon dioxide. Glycerol is also metabolized as an efficient energy source.

Waste water systems, for example those in the food service industry, typically incorporate a grease trap to trap grease and other contaminants from the passing flow of waste water and to store such contaminants for eventual removal from the trap. Typically, the grease trap is accessed periodically and the contaminants removed for eventual disposal. Grease and other contaminants often build up very quickly in such traps. If they are not removed in a timely fashion, the ability of the trap to operate efficiently, or at all, is seriously affected. When a trap is no longer functional, the contaminants will bypass the trap and flow into areas which are intended to be free from these contaminants. Specifically, the contaminants will either clog up the waste water system or will flow into the municipal sewer system in violation of local ordinances or state laws. Most grease traps require relatively large compartments, particularly if the associated food service facility operates on a large volume.

A variety of approaches have been developed to increase the required period between subsequent cleanings of a grease trap by increasing the biodegradation by microorganisms of grease in the trap. One approach to enhancing biodegradation of grease in a grease trap is to introduce chemicals or nutrients to the trap to aid naturally occurring bacteria or microorganisms in the trap. For example, U.S. Pat. No. 5,340,376 granted to Cunningham discloses a controlled-release nutrient source that adds nutrients at low levels to a bioremediation environment to enhance microorganism growth and activity and promote the effectiveness of the bioremediation in removing environmental contaminants. The nutrients are in the form of coated solid particles, each having a core of water soluble microorganism nutrients encapsulated in a release rate-controlling coating. The effectiveness of bioremediation of wastes by enhancing the growth of naturally occurring bacteria or microorganisms with the introduction of a controlled-release nutrient source is still hindered due to environmental fluctuations such as changes in temperature, pH, salinity, water and air supply, etc.

Another approach to enhancing biodegradation of grease in a grease trap is to introduce a structure upon which indigenous microorganisms can bind and grow, and thus effectively remain in the grease trap. For example, U.S. Pat. No. 4,925,564 and U.S. Pat. No. 4,670,149 both granted to Francis disclose a bacterial incubator device having an enclosure with a foraminous wall structure packed with high surface area elements such as spherical packing of a shape or size to multiply the solid bacterial growth surface area in a grease trap. The incubator is positioned at the interface of floating grease and water. Similarly, the effectiveness of bioremediation of wastes by enhancing the growth of naturally occurring bacteria or microorganisms with the introduction of a support structure is often hindered due to environmental fluctuations such as changes in temperature, pH, salinity, water and air supply, etc.

Still another approach to enhancing biodegradation of grease in a grease trap is to introduce additional microorganisms into the grease trap. For example, U.S. Pat. No. 5,271,829 granted to Heppenstall discloses a treatment system for waste water which includes a dispenser for introducing treatment material, a solution of bacteria, into a grease trap for the purpose of digesting the grease which is separated from waste water as it flows through the grease trap. The dispenser includes a housing having a compartment for holding a quantity of grease digesting material and a dispensing opening at the lower end of the compartment. A restricter is located at the dispensing opening permitting the digesting material to pass at a constant restrictive rate from the dispensing opening to the grease to be treated in a chamber of the grease-trap. The grease digesting material in the dispenser will naturally go through a four phase growth cycle (i.e., lag, exponential, stationary, and death, further described in detail in a Bacterial Growth Section below) which limits its effectiveness of enhancing the biodegradation of grease on an extended or continuous basis.

Another example of introducing additional microorganisms in to a grease trap is U.S. Pat. No. 5,225,083 granted to Pappas, et al. Pappas, et al. discloses a simple method that includes adding endemic bacterial microorganisms to one or more of the drain lines for ultimate introduction into the grease trap and biodegrading grease. Depending on the bacterial microorganisms growth cycle phases, the effectiveness of the biodegradation of grease by the microorganisms will vary.

Another approach to enhancing biodegradation of grease in a grease trap is to introduce enzymes into the grease trap to solubilize the grease. For example U.S. Pat. No. 4,940,539 granted to Weber discloses a grease trap comprising a housing having an inlet to receive waste water containing grease and an outlet. The waste water within the housing is heated by an electric heating element which is immersed in the waste water and the heating element is controlled by a thermostat to maintain a desired temperature of the water within a given range. An aqueous composition containing a mixture of enzymes and bacterial spores is introduced into the housing into contact with the waste water. The enzymes solubilize the grease while the bacteria spores biodegrade the grease. However, the ability of the bacteria to biodegrade waste will be delayed in that the bacterial spores first enter a lag phase requiring a period of time before entering an exponential growth phase in which to begin biodegradation of the waste.

Another example, U.S. Pat. No. 4,882,059 granted to Wong, et al. discloses a method for solubilizing particulate materials in waste water which comprises the steps of cultivating aerobic bacteria in the presence of oxygen in an activator solution containing a food source until the level of the food source drops below a predetermined level causing the bacteria to begin producing increased amounts of enzymes and thereafter contacting the activated bacteria and enzymes with the particulate materials under conditions which solubilize the waste. Another example, shown in U.S. Pat. No. 5,171,687 granted to Moller, et al., discloses an apparatus for culturing and delivering microbes for waste treatment in a flow system. The apparatus includes a container having a first and second chambers. The first chamber is maintained in a nutrient rich environment for the source microbial matter supported therein while the second chamber is nutrient deficient. Water is introduced into the first chamber at a predetermined rate and flows through an outlet into the second chamber. The outlet of the second chamber is directed to a flow system benefiting from the activity of the microbial matter. In both Wong and Moller, et al., it is believed that starving the bacteria of nutrients activates enzyme production therein to aid in solubilizing particulate materials in waste water. Although, the enzymes aid in solubilizing the grease, the bacteria will be ineffective in biodegrading the solubilized grease in that the bacteria being nutrient deficient will enter a stationary phase (if not death phase) necessitating that the bacteria enters a lag phase, requiring a period of time before the bacteria enters an exponential growth phase in which to begin to biodegrade the grease.

There is a need for a bio-augmentation system for use in a waste treatment facility in which the system maintains microorganisms in an active exponential growth and at a predetermined concentration, desirably a maximum concentration, and that further delivers active microorganisms on a continuous or periodic basis into contact with an environment containing wastes for effectively bio-augmenting the biodegradation of the wastes contained in the environment.

SUMMARY OF THE INVENTION

Accordingly it is an object of the present invention to provide, in a waste treatment facility, a bio-augmentation system that adjusts the environment to be treated to a condition that is more conducive to biodegradation of the treated waste by introduction of acclimated bacteria or microorganisms designed for that purpose.

It is another object of the present invention to provide a bio-augmentation system that maintains microorganisms in an active exponential growth and acclimated to an environment to be delivered, and deliver the microorganisms to an environment containing wastes for efficiently and quickly biodegrading the wastes.

It is also an object of the present invention to provide a bio-augmentation system that introduces microorganisms into an environment to be treated to ensure long-term maintaining, supplementing, and reconditioning of the bio-degradation process for peak performance or restarting the biodegradation process should the normal rate of biodegradation stall in the environment to be treated.

It is still another object of the present invention to provide a bio-augmentation system that injects microorganisms into a waste flow system, e.g., a grease trap, which greatly increases the normally required time between removal of accumulated grease.

It is still another object of the present invention to provide a bio-augmentation system for use in conjunction with a grease trap and which reduces the size of the required grease trap for effectively removing grease from waste water before discharge of the waste water into a municipal sewer system as permitted under local environmental ordinances or state laws.

It is yet another object of the present invention to provide a bio-augmentation system for use in waste treatment in which the system overcomes the problems hindering the effectiveness of biodegradation associated with environmental fluctuations such as changes in temperature, pH, salinity, water and air supplies, etc.

It is still another object of the present invention to provide a bio-augmentation system for use with various waste treatment facilities, such as drain lines, leach ponds, septic systems and lift stations, for bio-remediating waste water streams, and ground water and soil contamination.

It is a further object of the present invention to provide a bio-augmentation system for biological purification of wastes which is simple in construction and which is inexpensive, and which is capable of a long life of useful service with a minimum of maintenance.

It is an object of the present invention to provide a method for culturing and delivering microorganisms in exponential growth to an environment for biodegradation of wastes contained in the environment.

Certain of the foregoing and related objects are readily obtained in a bio-augmentation apparatus for containing a microorganism culture and delivering a supply of microorganisms to an environment containing wastes for bio-augmenting the biodegradation of the wastes, in which the apparatus comprises a first container having a bioreactor chamber for containing a microorganism culture and an operably connected controller. The controller includes a means for introducing a predetermined supply of water to the bioreactor chamber, and for introducing a predetermined supply of at least one of inorganic nutrients and organic nutrients to the bioreactor chamber, and means for removing a preselected supply of water, at least one of inorganic nutrients and organic nutrients, and microorganisms from the bioreactor chamber so that the controller is effective to maintain such microorganism culture in substantially exponential growth in the bioreactor chamber, and means for delivering such a removal preselected supply of water, at least one of inorganic nutrients and organic nutrients, and microorganisms in substantially exponential growth into contact with an environment containing wastes for biodegradation of the wastes.

Preferably, the bio-augmentation apparatus includes means for introducing a predetermined supply of oxygen to the bioreactor chamber. Desirably, the means for introducing a predetermined supply of water to the bioreactor chamber, and for introducing a predetermined supply of at least one of inorganic nutrients and organic nutrients to the bioreactor chamber, and the means for removing a preselected supply of water, at least one of inorganic nutrients and organic nutrients, and microorganisms from the bioreactor chamber so that the controller is effective to maintain the microorganisms in the bioreactor chamber in substantially exponential growth, is either periodically operable or continuously operable. Advantageously, the means for introducing a predetermined supply of water to the bioreactor chamber, and for introducing a predetermined supply of at least one of inorganic nutrients and organic nutrients to the bioreactor chamber, and the means for removing a preselected supply of water, at least one of inorganic nutrients and organic nutrients, and microorganisms from the bioreactor chamber, is operable to introduce and remove, respectively, substantially the same volumetric supplies.

In an preferred embodiment of the present invention, the bio-augmentation apparatus includes a second container having a second chamber for containing a supply of water and inorganic nutrients in which the second chamber is operably connected in fluid communication with the bioreactor chamber, and a third container having a third chamber for containing a supply of organic nutrients in which the third chamber is operably connected in fluid communication with the bioreactor chamber. The first container includes a circular bottom and an upwardly extending cylindrical side wall, the second container includes a circular bottom and an upwardly extending cylindrical side wall, and the third container includes a circular bottom and an upwardly extending cylindrical side wall.

Desirably, the first container is disposed within the second container, the third container is disposed within the bioreactor chamber, and the second chamber is annular in shape.

In another preferred embodiment of the present invention of the bio-augmentation apparatus, the means for introducing a predetermined supply of water to the bioreactor chamber, and for introducing a predetermined supply of at least one of inorganic nutrients and organic nutrients to the bioreactor chamber, includes a first pump operably connected in fluid communication between the bioreactor chamber and the second chamber, and the means for removing a preselected supply of water, at least one of inorganic nutrients and organic nutrients, and microorganisms and means for delivering the removed preselected supply of water, at least one of inorganic nutrients and organic nutrients, and microorganisms into contact with an environment containing wastes to be biodegraded, includes a second pump operably connected in fluid communication between the bioreactor chamber and the environment containing wastes to be biodegraded.

Desirably, the controller includes a timer and a regulator operably connected to the first pump and second pump to effectively maintain the microorganisms in substantially exponential growth in the bioreactor chamber.

Certain of the foregoing and related objects are also readily obtained in a method for bio-augmenting the biodegradation of wastes. The method includes the steps of: providing one of inorganic nutrients and organic nutrients to the microorganism culture, removing a preselected supply of water, at least one of inorganic nutrients and organic nutrients, and microorganisms from the microorganism culture so that the microorganism culture is maintained in substantially exponential growth, and delivering the removed preselected supply of water, at least one of inorganic nutrients and organic nutrients, and microorganisms into contact with an environment containing a waste for biodegrading the waste.

Preferably, the microorganisms are at least one of anaerobic and aerobic microorganisms, and the at least one inorganic nutrients and organic nutrients are substantially similar to wastes contained in the waste to be biodegraded so as to acclimate the microorganisms to the waste to be biodegraded. Advantageously, the microorganism culture is maintained in substantially exponential growth midway between a lag phase and a stationary phase. Desirably, the microorganism culture is maintained in a bioreactor chamber at a concentration of about 500 million cells/cubic centimeter to about 3 billion cells/cubic centimeter. More desirably, the microorganism culture is maintained in a bioreactor chamber at a concentration of about 2.5 billion cells/cubic centimeter.

Preferably, the step of introducing a predetermined supply of water and at least one of inorganic nutrients and organic nutrients to the microorganisms culture and the step of removing a preselected supply of water, at least one of inorganic nutrients and organic nutrients, and microorganisms from the microorganism culture so that the microorganism culture is maintained in substantially an exponential growth, are either periodically or continuously performed.

BRIEF DESCRIPTION OF THE DRAWINGS

Other objects and features of the present invention will become apparent from the following detailed description considered in connection with the accompanying drawings, which disclose several embodiments of the invention. It is to be understood that the drawings are to be used for the purpose of illustration only and not as a definition of the limits of the invention.

In the drawings, similar reference characters denote similar elements throughout the several views.

DETAILED DESCRIPTION OF THE INVENTION

Apparatus

Figure 1:
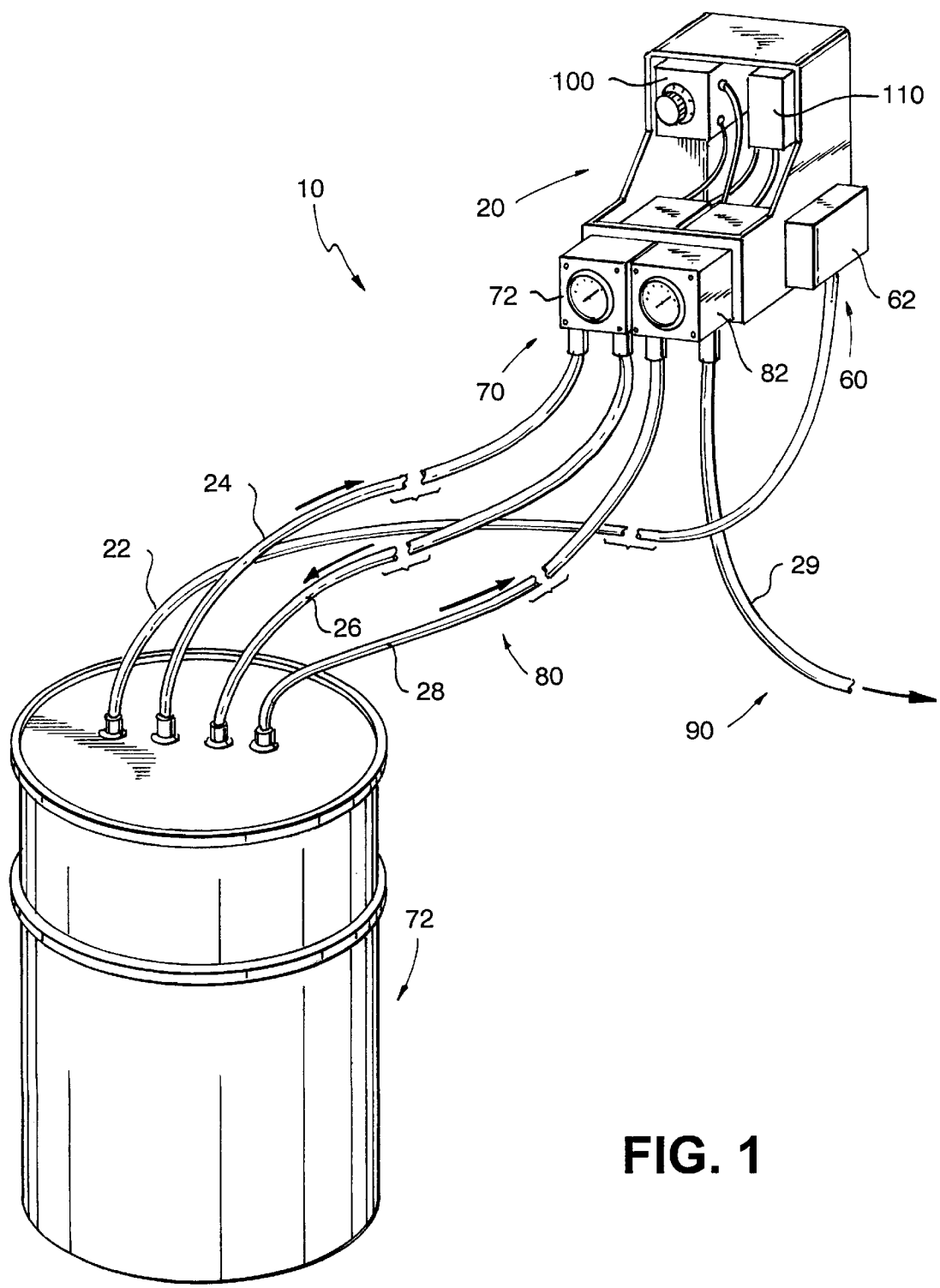
FIG. 1 is a perspective view of a preferred embodiment of an apparatus of the present invention which generally includes a bioreactor operably connected to a controller.

Turning now to the drawings and in particular to FIG. 1, therein illustrated is a bio-augmentation apparatus 10 embodying the present invention. Apparatus 10 generally includes a bioreactor 12 for containing a microorganism culture (not shown) in which bioreactor 12 is operably connected to a controller 20 via tubes 22, 24, 26, 28 for effectively maintaining the microorganism culture in exponential growth and for delivering microorganisms via tube 29 to an environment containing wastes for bio-augmenting the biodegradation of the wastes, e.g., grease in a grease trap or septic tank (not shown). The operation of apparatus 10 is explained in greater detail in an Operation Section below.

Figure 2:
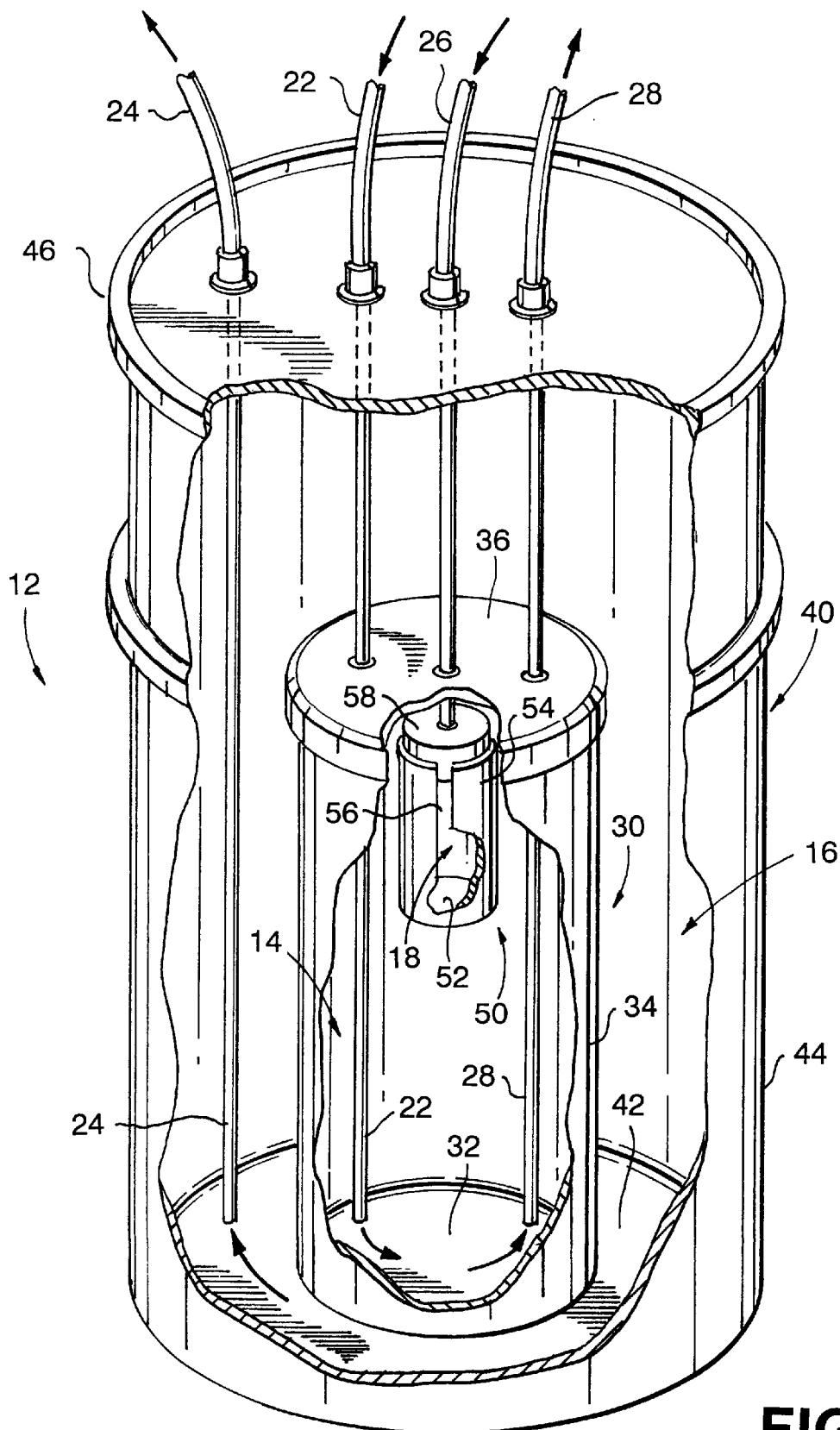
FIG. 2 is an enlarged perspective view, partially broken away, of the bioreactor of FIG. 1.

Referring to FIG. 2, bioreactor 12 includes a first container 30 having a circular bottom 32 and an upwardly extending cylindrical side wall 34. A removable lid 36 is attached to the upper end of side wall 34 and closes container 30. Surrounding first container 30 is a second container 40 having a circular bottom 42 and an upwardly extending cylindrical side wall 44. A removable lid 46 is attached to the upper end of side wall 44 and closes container 40.

Defined within first container 30 is a cylindrical bioreactor chamber 14 for containing a microorganism culture (not shown). Defined between first container 30 and second container 40 is an annular storage or second chamber 16 for containing a supply of water and inorganic nutrients, such as potassium phosphate, ammonium nitrite and calcium chloride.

Preferably, containers 30 and 40 are fabricated from a plastic material that is nontoxic and does not react with the microorganisms, such as polyethylene or polyvinyl chloride. Although bioreactor 12 is shown in a compact configuration, it will be appreciated that containers 30 and 40 can be square or rectangularly shaped and disposed in side by side relationship.

A third container 50 having a third chamber 18, for containing a supply of organic nutrients (not shown) or carbon source such as compacted dry potassium-oleate powder or other water soluble salts of fatty acids, is disposed within bioreactor chamber 14 and supported above the microorganism culture. Desirably, the supply of organic nutrients is similar to that of the waste to be biodegraded so as to acclimate the microorganisms in the microorganism culture (not shown) to the waste to be biodegraded. Specifically, container 50 is cylindrically shaped having an a circular bottom 52 and an upwardly extending cylindrical side wall 54. The upper end of cylindrical side wall 54 receives a rubber stopper 58 that attaches to tube 26 for receiving a supply of water and inorganic nutrients. A longitudinally extending slit 56 in container 50 permits organic nutrients contained in chamber 18 to be dissolved by a supply of water and inorganic nutrients as they pass through chamber 18 and discharge into bioreactor chamber 14. Again, although bioreactor 12 is shown in a compact configuration, it will be appreciated that container 50 need not be placed inside bioreactor chamber 14 but could consist of a separate stand alone unit or alternatively the supply of organic nutrients could be suitably incorporated in-line with tube 26.

Referring again to FIG. 1, controller 20 effectively maintains the microorganism culture in substantially exponential growth in bioreactor 12 and delivers active microorganisms to an environment to be treated. Specifically, controller 20 controls delivery of a predetermined supply of water, inorganic nutrients, organism nutrients and air into bioreactor 12 and controls removal of a preselected supply or water, inorganic nutrients, organic nutrients and active microorganisms from bioreactor 12.

Means 60 for introducing a predetermined supply of oxygen to bioreactor 12 includes an air pump 62 connected to tube 22. Specifically, tube 22 is connected at one end to air pump 62, and as shown in FIG. 2, the opposite end passes through cover 36 and cover 46 so that the opposite end is positioned adjacent bottom 32 of container 30 in bioreactor chamber 14.

Referring again to FIG. 1, means 70 for introducing a predetermined supply of water (not shown) from second chamber 16 (FIG. 2) to bioreactor chamber 14 (FIG. 2), and for introducing a predetermined supply of organic nutrients (not shown) from third chamber 18 (FIG. 2) to bioreactor chamber 14 (FIG. 2), includes a first pump 72, tubes 24 and 26, timer 100 and regulator 110. Specifically, as shown in FIG. 2, tube 24 has a free end disposed adjacent bottom 32 of container 30 for receiving a predetermined supply of water and inorganic nutrient contained in second chamber 16 and the other end of tube 24 is attached to an input port on pump 72 (FIG. 1). An output port of pump 72 (FIG. 1) is attached to one end of tube 26 and the opposite end of tube 26 passes through lid 36, lid 46 for connection to stopper 58 in container 50.

As shown in FIG. 1, the amount or flow of water removed from second chamber 16 (FIG. 2) and discharged into bioreactor chamber 14 (FIG. 2) is controlled by timer 100 operably connected via wires to pump 72 to turn pump 72 on and off, and regulator 110 is operably connected via wires to pump 72 to adjust the supply of electrical energy to pump 72 thereby to control the speed of pump 72 and thus the flow rate of water when pump 72 is activated. Although, water can be supplied from a municipal water source, it is desirable to include in the supply of water various inorganic nutrients.

Means 80 for removing water, inorganic nutrients, organic nutrients, and microorganisms from bioreactor 12 so as to effectively maintain the remaining microorganism culture in exponential growth includes a second pump 82, tube 28, timer 100 and regulator 110. Specifically, as shown in FIG. 2, tube 28 has a free end disposed adjacent bottom 42 of container 40 for receiving a preselected supply of water, inorganic nutrients, organic nutrients, and microorganisms contained in bioreactor chamber 14 and an opposite end of tube 28 is attached to an input port on pump 82 (FIG. 1).

Referring again to FIG. 1, means 90 for contacting the removal preselected water, inorganic nutrients, organic nutrients, and microorganisms delivered via tube 28 of means 80 with an environment containing wastes, includes pump 82 and tube 29. Specifically, as shown in FIG. 2, tube 29 has one end attached to an output port on pump 82 (FIG. 1) and an opposite end operably connected to a drain or trap (not shown) for discharging a preselected amount of the contents of bioreactor chamber 14 containing water, inorganic nutrients, organic nutrients, and microorganisms.

The amount of flow of water, inorganic nutrients, organic nutrients, and microorganisms, from bioreactor chamber 14 (FIG. 2) to a trap (not shown) is controlled by timer 100 operably connected via wires to pump 82 to turn pump 82 on and off, and regulator 110 operably connected via wires to pump 82 to adjust the supply of electrical energy to pump 82 thereby to control the speed of pump 82 and thus the flow rate of water, inorganic nutrients, organic nutrients, and microorganisms, when pump 82 is activated. Air pump 62, timer 100 and regulator 100 are operably connected to an electrical outlet, preferably 120 volts A.C. (not shown).

Bacterial Growth

A key factor of the present invention is the ability to retain the acclimated microorganism culture in exponential growth (also known as logarithmic growth) where the microorganisms, i.e., the number of cells, increase in a direct proportion to time or divide at a constant rate, and thus are most active, and to deliver active microorganisms to an environment to be treated.

Figure 3:
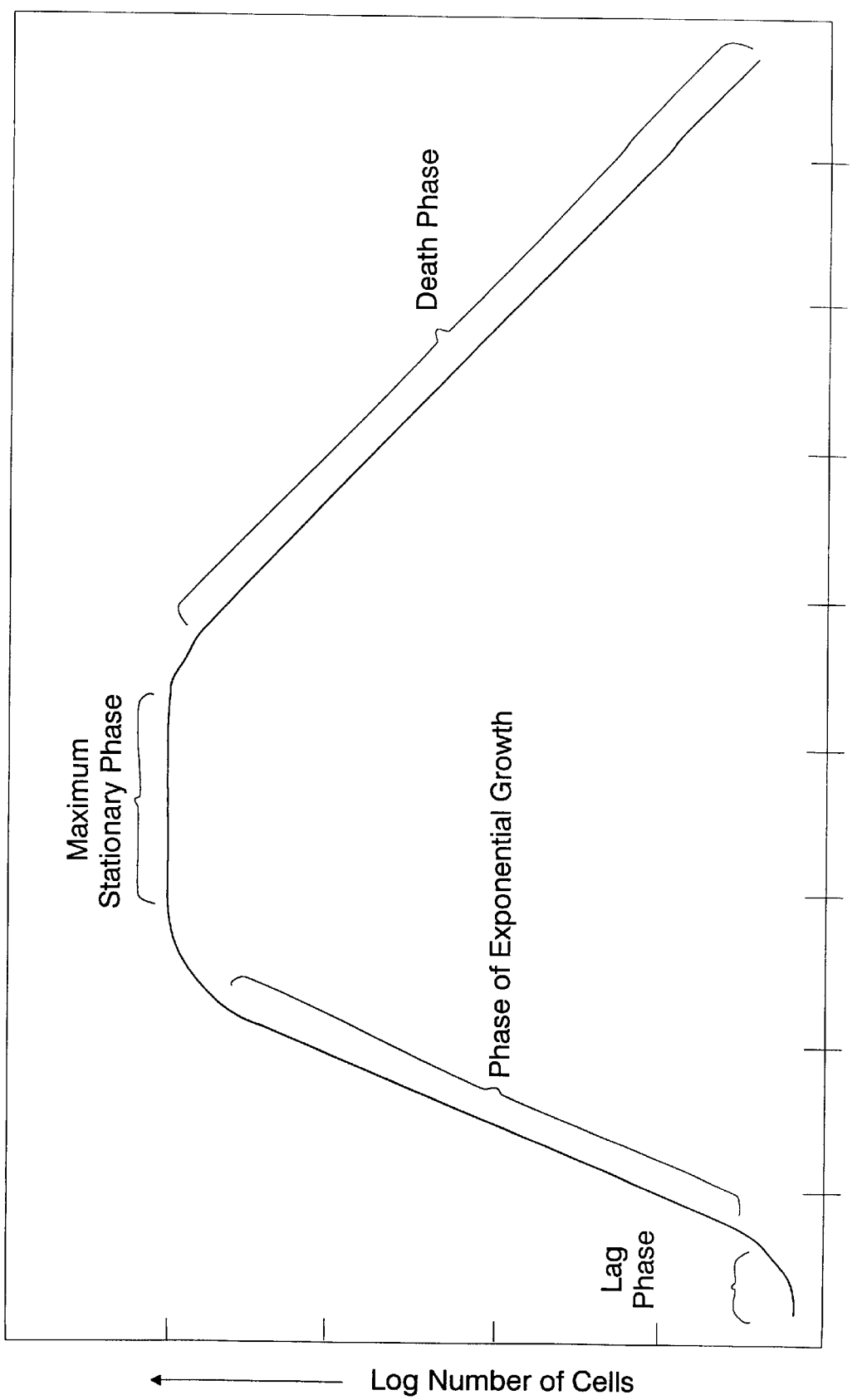
FIG. 3 is a graphical representation of a typical four phase bacterial growth cycle (i.e., lag, exponential, stationary, and death) of a microorganism culture in which no additional culture medium is added.

Specifically, referring to FIG. 3, therein is illustrated a typical growth cycle showing four distinct phases in the cycle of a culture under constant condition, i.e. no additional culture medium (organic and inorganic nutrients) are added for the growth of microorganisms in the culture. The four illustrated growth phases are; lag, exponential, stationary, and death. In the lag phase the number of cells does not increase and the cells are preparing for active growth. Eventually, cell division occurs and an exponential growth phase is reached. Finally, either some nutrients become exhausted or some toxic metabolic products accumulate, and the growth rate decreases and growth ceases.

In the present invention it is desired to retain the acclimated microorganism culture in exponential growth where the microorganisms are most active, and to deliver the active microorganisms to an environment to be treated in which the microorganisms immediately begin to biodegrade the waste.

It is not desirable to have the microorganisms delivered to an environment to be treated in which the microorganisms are in a lag phase requiring a period of time before the microorganisms reach exponential growth in which to begin biodegradation of the waste. For example, if the environment to be treated is a grease trap having a periodic or constant fluid flow, the microorganisms will be washed away or removed from the grease trap before being able to biodegrade the waste.

Nor is it desirable to have the microorganisms delivered to an environment to be treated in which the microorganisms are in a stationary phase and become stressed which upon delivery of the microorganisms into an environment to be treated require the microorganisms to enter a lag phase and require a period of time before entering exponential growth. Again, for example, if the environment to be treated is a typical grease trap having a periodic or constant fluid flow the microorganisms will be washed away or removed from the grease trap before being able to biodegrade the waste.

Operation

The operation of the present invention will be explained with respect to FIG. 4, a diagrammatical illustration of bio-augmentation apparatus 10 for culturing microorganisms in exponential growth and for delivering microorganisms to an environment containing wastes for bio-augmenting the biodegradation of the wastes, e.g., grease in a grease trap 120.

In set-up of apparatus 10, covers 36 and 46 of bioreactor 12, shown in place, are removed and an initial microorganism culture 200 consisting of microorganisms and a culture medium of water, inorganic nutrients and organic nutrients, is placed in bioreactor chamber 14 of first container 30. Preferably aerobic or anaerobic bacteria, which are either naturally occurring or developed specifically for biodegradation of the specific waste in a environment to be treated, is suitable for use with the present invention.

A predetermined supply of water or water and inorganic nutrients 210 is placed in second chamber 16 of second container 40. A supply of dissolvable organic nutrients 220 is packed inside container 50. Covers 36 and 46 are replaced.

The free end of tube 29 is connected to generally the starting point of the waste stream for example a drain (not shown) leading into a grease trap 120 or directly into grease trap 120.

Once the microorganism culture 200 reaches exponential growth, controller 20 is activated to maintain the microorganism culture in exponential growth and deliver microorganisms to an environment to be treated in which the microorganisms are exponentially growing, and thus are at peak performance for biodegrading the waste contained in the environment to be treated.

Referring again to FIG. 4, specifically, controller 20 is set-up to control the rate of water, inorganic nutrients, and organic nutrients into bioreactor chamber 14 and control the rate of water, inorganic nutrients, organic nutrients, and microorganisms out of bioreactor chamber 14 and delivered to the environment to be treated, e.g., grease trap 120. A number of variables are involved in maintaining the microorganism culture in exponential growth. Such variables are the type of microorganism and its specific growth rate, the volume of the culture, the initial culture medium, the rate of introduction of water, inorganic nutrients, and organic nutrients into the microorganism culture, and the rate of removal of water, inorganic nutrients, organic nutrients, and microorganisms from the microorganism culture which is delivered to an environment to be treated.

Given a certain type of microorganism having a specific growth rate constant, a certain volume of culture, and an initial culture medium, the microorganism culture can be monitored to determine the number of cells in the microorganism culture, i.e., periodically conventionally measuring the optical density of samples taken from the culture. The microorganism culture will go through a lag, exponential and stationary phases. By setting-up controller 20, the rate of introduction of water, inorganic nutrients, and organic nutrients into the microorganism culture, and the rate of removal of water, inorganic nutrients, organic nutrients, and microorganisms from the microorganism culture and delivered to an environment to be treated can be adjusted to maintain the microorganism culture in exponential growth before the microorganism culture reaches the stationary phase.

The rate of introduction of water, inorganic nutrients, and organic nutrients into the microorganism culture, and the rate of removal of water, inorganic nutrients, organic nutrients, and microorganisms from the microorganism culture and delivered to an environment to be treated can be either at a continuous rate or accomplished periodically. Desirably, the rate (volume per time) of the introduction and removal will be substantially volumetrically the same whether controller 20 is operated in a continuous or periodic mode. That is, pumps 72 and 82 will be operated simultaneously.

To increase the activity in bioreactor chamber 14, a mixer 140 such as a stirrer or paddle can be operably installed in bioreactor chamber 14. In addition, a mixer 145 such as a stirrer or paddle can also be placed in grease trap 120 to increase the contact of microorganisms to the grease.

EXAMPLE

Figures 5A, 5B:
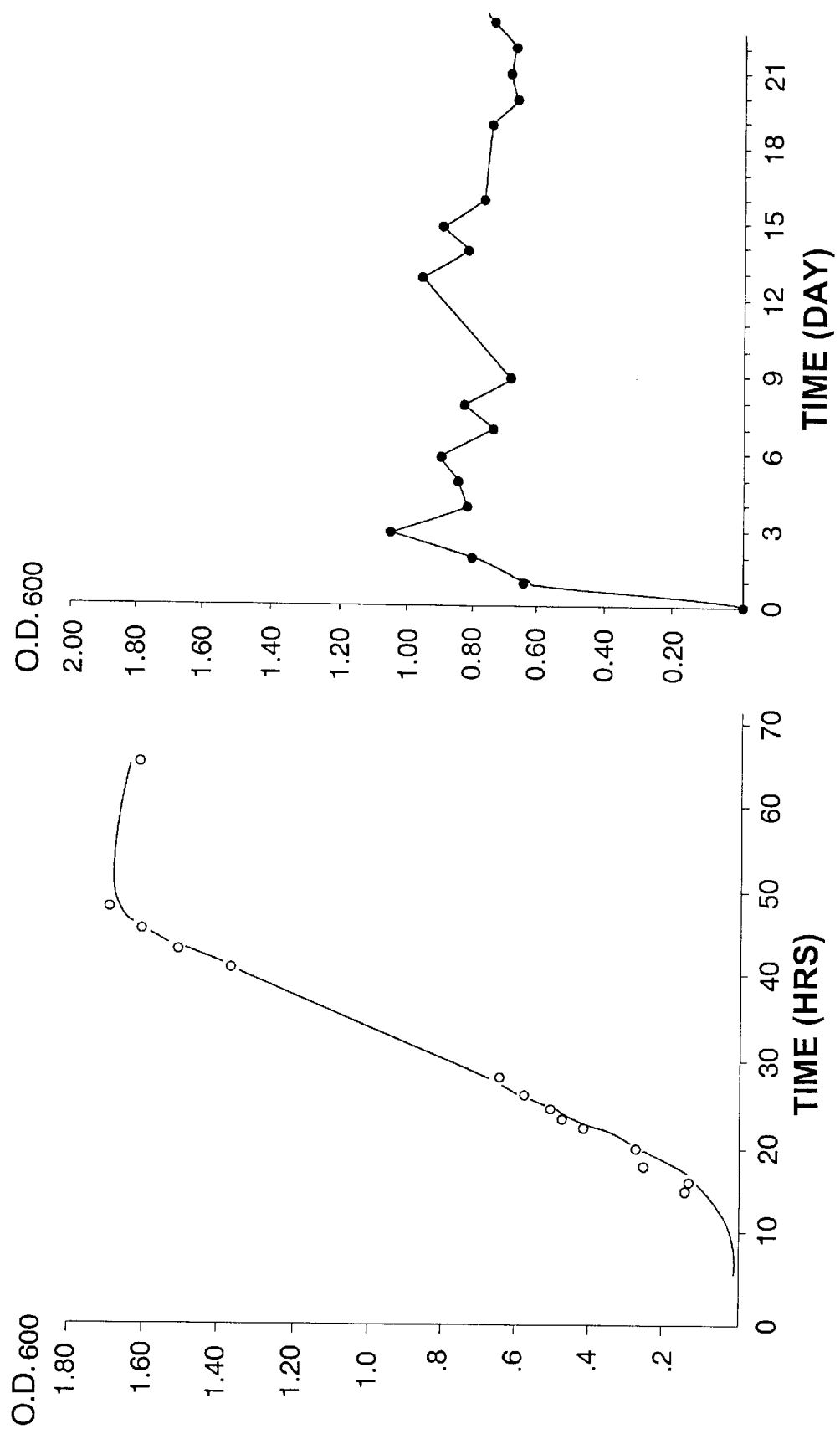
FIGS. 5(a) and 5(b) are graphical results using optical density measuring means for periodically sampling (a) a microorganism culture which shows the various lag, exponential and stationary growth cycle phases of the microorganism culture and (b) a microorganism culture maintained in the bio-augmentation system of FIG. 1 in which the microorganism culture is maintained in exponential growth.
Figure 6:
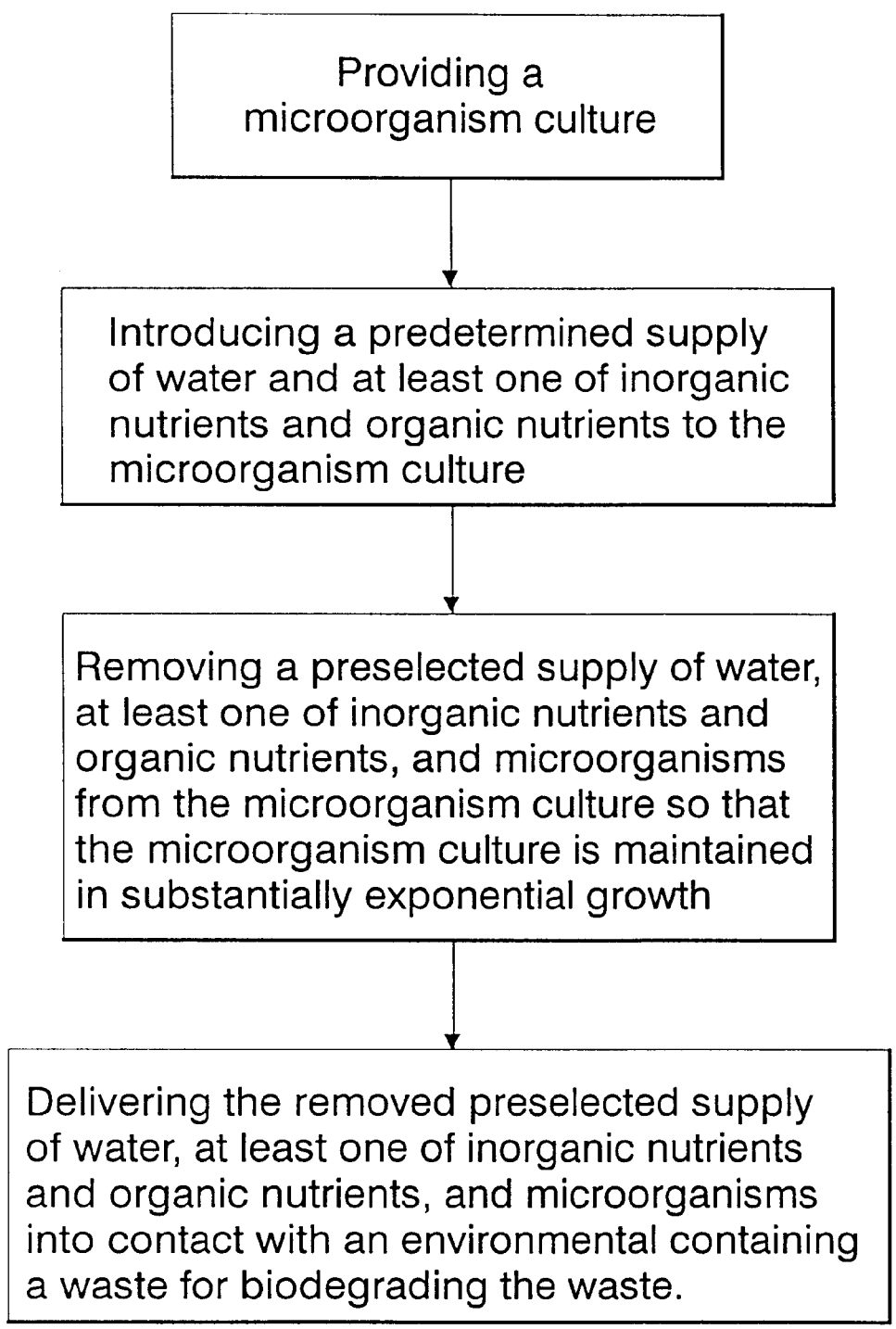
FIG. 6 is a flow chart illustrating the method of the present invention.

Referring to FIG. 5($a$), there is graphically illustrated the optical density versus time results of an initial three day experiment that determined the typical growth cycle of a microorganism culture using optical density measuring means of periodic sampling of the microorganism culture. The microorganism culture consisted of Number 700 bacteria mixture by Sybron Chemicals Inc. A Hewlett Packard 8452A Diode Array Spectrophotometer operating at a 600 nanometer wavelength of light was used to determine the optical density of samples removed from the culture.

Referring now to FIGS. 1 and 5($b$), the graphically illustrated results of optical density versus time, for a microorganism culture in bio-augmentation apparatus 10, which after approximately three days, was allowed to reach a cell density midway between its lower and upper exponential growth phase limits as determined and illustrated in FIG. 5($a$). Upon the microorganism culture reaching a cell density approximately midway between its lower and upper exponential growth phase limits, controller 20 was activated to maintain the microorganism culture at substantially such a cell density and deliver microorganisms to an environment to be treated for a period of over approximately twenty one days.

Figure 4:
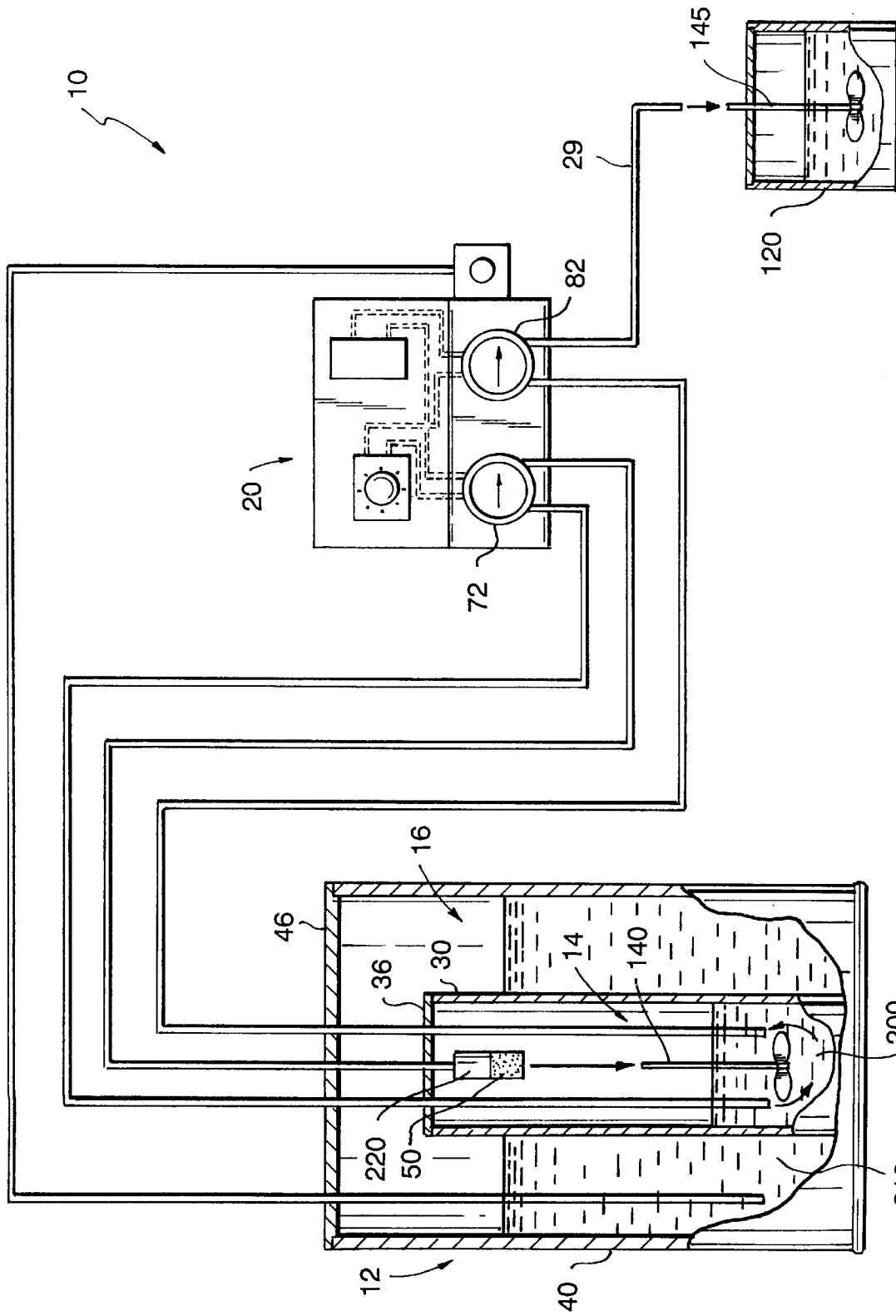
FIG. 4 is a diagrammatic illustration of the bio-augmentation apparatus of FIG. 1.

Referring to FIGS. 4 and 5($b$), during the approximately twenty one days, every 4 hours about 200 cubic centimeters of water, inorganic nutrients and organic nutrients, was added to the microorganism culture and approximately 200 cubic centimeters of water, inorganic nutrients, organic nutrients and microorganisms was removed from the microorganism culture and delivered to a grease trap containing grease to be biodegraded. The water containing inorganic nutrients consisted of potassium phosphate, ammonium nitrite, calcium chloride and magnesium chloride. Specifically, the following is a listing of the relative amounts of water and inorganic nutrients:

$H_2O$—1 liter $KH_2PO_4$—1 gram $K_2HPO_4$—1 gram $NH_4NO_3$—1 gram $CaCl_2$—0.002 gram $MgCl_2$—0.002 gram A typical grease trap 120 without the use of bio-augmentation apparatus 10 requires grease trap 120 to be cleaned every thirty (30) days, and a typical grease trap 120 with the use of bio-augmentation apparatus 10 in operation requires a grease trap to be cleaned only once a year (365 days). Preferably, the microorganism culture is maintained in a bioreactor chamber at a concentration of about 500 million cells/cubic centimeter to about 3 billion cells/cubic centimeter. More preferably the microorganism culture is maintained in a bioreactor chamber at a concentration of about 2.5 billion cells/cubic centimeter.

It will be appreciated that microorganism culture 200 can be operated at a greater cell density. However, operating at too great a cell density risks having the microorganism culture enter a stationary phase should not enough water, inorganic nutrients or organic nutrients be timely introduced. Too low a cell density does not produce enough microorganisms for effective and optimum biodegrading of wastes. Desirably, a cell density midway between its lower and upper limits of its exponential growth phase is maintained in bioreactor 12.

Method

The method according to the present invention for bio-augmenting the biodegradation of wastes, comprising the steps of: providing a microorganism culture, introducing a predetermined supply of water and at least one of inorganic nutrients and organic nutrients to the microorganism culture, removing a preselected supply of water, at least one of inorganic nutrients and organic nutrients, and microorganisms from the microorganism culture so that the microorganism culture is maintained in substantially exponential growth, and delivering the removed preselected supply of water, at least one of inorganic nutrients and organic nutrients, and microorganisms into contact with an environment containing a waste for biodegrading the waste.

It will be appreciated that the present invention is ideally suitable for use in bio-augmenting the biodegradation of grease in a grease trap, however, the present invention is also amenable to bioremediation of other waste or waste streams such as lagoons, aeration ponds, soil and ground water.

In addition, various means for maintaining and delivering the microorganisms in an exponential growth rate such as electrically or pneumatically operated solenoids or gravity flow means are equally applicable for use in such a bio-augmentation system of the present invention.

While only several embodiments of the present invention have been shown and described, it is obvious that many changes and modification may be made thereunto without departing from the spirit and scope of the invention.

What is claimed is:

1. A method for controlling the accumulation of a predetermined waste product thereby maintaining fluid flow in a grease trap, comprising:

a) providing a portable apparatus adapted for maintaining a substantial percentage of the members of a microbial culture in log-phase growth;

b) growing a microbiological culture in the apparatus of step a) at the site of a grease trap to be maintained in the presence of an organic nutrient chemically similar to a waste product the accumulation of which is to be controlled;

c) periodically discharging an amount of the microbiological culture of step b) into the grease trap, the amount being effective to control the accumulation of the predetermined waste product thereby maintaining fluid flow.

2. The method of claim 1 wherein the predetermined waste product is selected from the group consisting of fat and grease.

3. The method of claim 1 wherein the organic nutrient similar to the predetermined waste product is a water soluble fatty acid.

4. The method of claim 1 wherein the organic nutrient is potassium-oleate.

\* \* \* \* \*